(12) United States Patent
Flores et al.

(10) Patent No.: US 11,364,062 B2
(45) Date of Patent: Jun. 21, 2022

(54) MATERIAL DELIVERY SURGICAL DEVICE

(71) Applicant: Spinal Elements, Inc., Carlsbad, CA (US)

(72) Inventors: Markanthony Flores, Chula Vista, CA (US); Daniel Zatta, Vista, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 23 days.

(21) Appl. No.: 15/679,916

(22) Filed: Aug. 17, 2017

(65) Prior Publication Data

US 2018/0125558 A1    May 10, 2018

Related U.S. Application Data

(60) Provisional application No. 62/376,835, filed on Aug. 18, 2016.

(51) Int. Cl.

| *A61B 17/58* | (2006.01) |
| *A61B 17/60* | (2006.01) |
| *A61F 2/00* | (2006.01) |
| *A61B 17/88* | (2006.01) |
| *A61B 90/00* | (2016.01) |
| *A61B 17/00* | (2006.01) |
| *A61F 2/46* | (2006.01) |

(52) U.S. Cl.
CPC ...... *A61B 17/8822* (2013.01); *A61B 17/8811* (2013.01); *A61B 17/8819* (2013.01); *A61B 17/8833* (2013.01); *A61B 17/00491* (2013.01); *A61B 2017/0023* (2013.01); *A61B 2017/00367* (2013.01); *A61B 2017/00407* (2013.01); *A61B 2017/00477* (2013.01); *A61B 2090/062* (2016.02); *A61B 2090/0807* (2016.02); *A61B 2217/005* (2013.01); *A61F 2/4601* (2013.01)

(58) Field of Classification Search
None
See application file for complete search history.

(56) References Cited

U.S. PATENT DOCUMENTS

| 4,338,925 A | 7/1982 | Miller |
| 4,405,249 A | 9/1983 | Scales |
| 4,546,767 A | 10/1985 | Smith |
| 4,671,263 A | 6/1987 | Draenert |
| 4,744,494 A | 5/1988 | Seager et al. |
| 4,815,454 A | 3/1989 | Dozier, Jr. |
| 4,994,065 A | 2/1991 | Gibbs et al. |
| 5,052,243 A | 10/1991 | Tepic |
| 5,082,243 A | 1/1992 | Berglund et al. |
| 5,431,654 A | 7/1995 | Nic |
| 5,697,932 A | 12/1997 | Smith et al. |

(Continued)

FOREIGN PATENT DOCUMENTS

WO    2008/080590    10/2008

*Primary Examiner* — Sameh R Boles

(57) ABSTRACT

Medical devices for injecting materials into patients are disclosed. The devices can include a body having a handle and a lever. The devices can also include a delivery tube comprising a passageway along a longitudinal axis and a nozzle with an opening, the delivery tube configured to couple with a distal end of the body. A driving rod can be inserted into the body and extend into the passageway, such that the lever can move the driving rod distally when the lever is actuated toward the handle. Methods of using the material delivery device are also disclosed.

17 Claims, 10 Drawing Sheets

(56) References Cited

U.S. PATENT DOCUMENTS

| | | |
|---|---|---|
| 6,045,555 A | 4/2000 | Smith et al. |
| 6,142,998 A | 11/2000 | Smith et al. |
| 6,309,395 B1 | 10/2001 | Smith et al. |
| 6,395,007 B1 | 5/2002 | Bhatnagar et al. |
| 6,439,439 B1 | 8/2002 | Rickard et al. |
| 6,494,868 B2 | 12/2002 | Amar |
| 6,719,761 B1 * | 4/2004 | Reiley ................ A61B 17/8811 604/93.01 |
| 7,004,945 B2 | 2/2006 | Boyd et al. |
| 7,014,640 B2 | 3/2006 | Kemppainen et al. |
| 7,112,205 B2 | 9/2006 | Garrison |
| 7,641,664 B2 | 1/2010 | Pagano |
| 7,677,418 B2 | 3/2010 | Henniges et al. |
| 7,713,273 B2 | 5/2010 | Krueger et al. |
| 7,811,291 B2 | 10/2010 | Liu et al. |
| 7,887,543 B2 | 2/2011 | Sand et al. |
| 8,034,088 B2 | 10/2011 | Pagano |
| 8,038,682 B2 | 10/2011 | McGill |
| 8,128,633 B2 | 3/2012 | Linderman et al. |
| 8,308,805 B2 | 11/2012 | Lynn et al. |
| 8,529,576 B2 | 9/2013 | Krueger et al. |
| 8,597,301 B2 | 12/2013 | Mitchell |
| 8,685,031 B2 | 4/2014 | Kleiner et al. |
| 8,721,600 B2 | 5/2014 | Henniges et al. |
| 8,932,295 B1 | 1/2015 | Greenhalgh |
| 8,945,137 B1 * | 2/2015 | Greenhalgh ..... A61B 17/00234 606/99 |
| 9,173,694 B2 | 11/2015 | Kleiner |
| 9,216,096 B2 | 12/2015 | Lynn et al. |
| 9,456,830 B2 | 10/2016 | Greenhalgh |
| 9,504,508 B2 | 11/2016 | Beyar et al. |
| 9,526,551 B2 | 12/2016 | Linderman et al. |
| 9,649,203 B2 | 5/2017 | Lynn et al. |
| 9,655,748 B2 | 5/2017 | Greenhalgh et al. |
| 9,668,881 B1 | 6/2017 | Greenhalgh |
| 10,195,053 B2 | 2/2019 | Kleiner et al. |
| 10,405,905 B2 | 9/2019 | Greenhalgh |
| 2005/0128867 A1 | 6/2005 | Henniges et al. |
| 2010/0249720 A1 | 9/2010 | Biyani et al. |
| 2011/0218513 A1 * | 9/2011 | Walker ............... A61B 17/8816 604/500 |
| 2013/0131683 A1 | 5/2013 | Shah et al. |
| 2016/0331443 A1 * | 11/2016 | Phan ................. A61B 18/1477 |

* cited by examiner

MATERIAL DELIVERY SURGICAL DEVICE

CROSS-REFERENCE TO RELATED APPLICATIONS

The present application claims priority benefit under 35 U.S.C. § 119(e) of U.S. Provisional Application No. 62/376,835 filed Aug. 18, 2016, the content of which is incorporated by reference herein in its entirety.

BACKGROUND

Field

The present application relates generally to surgical devices, and more particularly to surgical devices for delivering fusion-promoting material to a surgical site.

Background

The spine is a flexible structure that extends from the base of the skull to the tailbone. The weight of the upper body is transferred through the spine to the hips and the legs. The spine contains a plurality of bones called vertebrae. The vertebrae are hollow and stacked one upon the other, forming a strong hollow column for support. The hollow core of the spine houses and protects the nerves of the spinal cord. Each vertebra is separated from the vertebra above or below by a cushion-like, fibrocartilage called an intervertebral disc. The discs act as shock absorbers, cushioning the spine, and preventing individual bones from contacting each other. In addition, intervertebral discs act as a ligament that holds vertebrae together. Intervertebral discs also work with the facet joint to allow for slight movement of the spine. Together, these structures allow the spine to bend, rotate and twist.

The spinal structure can become damaged as a result of degeneration, dysfunction, disease and or trauma. More specifically, the spine may exhibit disc collapse, abnormal curvature, asymmetrical disc space collapse, abnormal alignment of the vertebrae and general deformity, which may lead to imbalance and tilt in the vertebrae. This may result in nerve compression, disability and overall instability and pain. If the proper shaping or curvature are not present due to scoliosis, neuromuscular disease, cerebral palsy, or other disorder, it may be necessary to straighten or adjust the spine into a proper curvature with surgery to correct these spinal disorders.

Some ailments of the spine result in degeneration of the spinal disc in the intervertebral space between adjacent vertebrae. Disc degeneration can cause pain and other complications. Conservative treatment can include non-operative treatment requiring patients to adjust their lifestyles and submit to pain relievers and a level of underlying pain. Operative treatment options include disc removal. This can relieve pain in the short term, but also often increases the risk of long-term problems and can result in motor and sensory deficiencies resulting from the surgery. Disc removal and more generally disc degeneration disease are likely to lead to a need for surgical treatment in subsequent years.

Another treatment option includes fusion, which is a surgical method wherein two or more vertebrae are joined together (fused) by way of interbody implants, sometimes with bone grafting, to form a single bone. The current standard of care for interbody fusion requires surgical removal of all or a portion of the intervertebral disc. After removal of the intervertebral disc, the interbody implant is implanted in the interspace to correct disc space collapse between adjacent vertebra, resulting in spinal fusion of the adjacent vertebra. In many cases, the fusion is augmented by a process called fixation. Fixation refers to the placement of screws, rods, plates, or cages to stabilize the vertebrae so that fusion can be achieved. The fusion or fixation will minimize or substantially eliminate relative motion between the fixed or fused vertebrae.

Fusion-promoting material has been shown to provide faster and improved osseointegration of the implant with the native bone and tissue. Oftentimes, fusion-promoting material is placed into and around the interbody implant to expedite and enhance the growth of bone material in the intervertebral space. The fusion-promoting material can be packed into the interbody implant before or after implantation. Additional fusion-promoting material can be packed around the implant to fill voids around the implant at the surgical site.

SUMMARY

An aspect of at least one of the embodiments disclosed herein includes a device for injecting materials into a patient, the device including a body comprising a handle, a lever, a collar and a cavity inside the body. The device can further include a delivery tube comprising a passageway along a longitudinal axis and a nozzle with a lateral opening, the delivery tube configured to releasably couple to the collar at a distal end of the body. A driving rod can be configured to be inserted from a proximal end of the body and extend through the cavity and into the passageway. In some embodiments, the collar is configured to rotate the delivery tube about the longitudinal axis. The lever can be configured to move the driving rod distally toward the delivery tube when the lever is actuated toward the handle.

An aspect of at least one of the embodiments disclosed herein includes a device for injecting materials into a patient, the device including a body having a handle and a lever. The device can also include a delivery tube with a passageway along a longitudinal axis and a nozzle with an opening, the delivery tube configured to couple with a distal end of the body. A driving rod can be configured to be inserted into the body and extend into the passageway. In some embodiments, the delivery tube is configured to rotate about the longitudinal axis. In some embodiments, the lever is configured to move the driving rod distally when the lever is actuated toward the handle.

The passageway of the delivery tube can be configured to be filled with fusion-promoting material. In some embodiments, the opening in the nozzle is a lateral opening. In some embodiments, the nozzle has an angled inner surface.

One or more of the delivery tube and driving rod can be at least partially flexible. The driving rod can have a plurality of ratchet teeth that are engaged by an advancement mechanism coupled to the lever. The device can further include a gripping element coupled to the lever that is configured to grab the driving rod when the lever is actuated. In some embodiments, the delivery tube and driving rod are disposable. The driving rod can be configured to move unidirectionally in the distal direction. In some embodiments, the driving rod includes at least one channel configured to align with at least one tab on the body. The delivery tube can further include indications representing the depth of insertion of the delivery tube into a patient.

An aspect of at least one of the embodiments disclosed herein includes a kit for injecting materials into a patient, the kit including a delivery tube with a passageway along a longitudinal axis with an opening at both ends of the passageway. A funnel can be configured to couple with an end of the delivery tube and a plug can be configured to block one of the openings of the delivery tube. The kit can include a ramrod with a shaft that is configured to fit in the passageway of the delivery tube.

The kit can further include a body with a handle and a lever. A driving rod can be configured to be inserted into the body and extend through the body. In some embodiments, the delivery tube is configured to releasably couple to a distal end of the body and be rotatable about the longitudinal axis while coupled to the body. In some embodiments, the lever is configured to move the driving rod distally into the passageway of the delivery tube when the lever is actuated toward the handle.

The body can further include a collar configured to rotate the delivery tube about the longitudinal axis. In some embodiments, one or more of the delivery tube and driving rod are at least partially flexible. In some embodiments, the delivery tube and driving rod are disposable.

At least one of the openings in the delivery tube can be a lateral opening. The passageway of the delivery tube can be configured to be filled with fusion-promoting material. The ramrod can be configured to push the fusion-promoting material through the funnel into the passageway. In some embodiments, at least a portion of the ramrod is flexible. In some embodiments, the funnel has a bent funnel stem.

An aspect of at least one of the embodiments disclosed herein includes a method of injecting materials into a patient. The method can include coupling a delivery tube on a distal portion of a body, wherein the delivery tube is filled with fusion-promoting material. The method can include inserting a driving rod into the body, wherein the driving rod is configured to fit in the delivery tube. A nozzle of the delivery tube can be placed in the patient, the nozzle having an exit opening. In some embodiments, the method includes manipulating a collar to rotate the delivery tube and direct the exit opening in a desired direction. A lever can be actuated to advance the driving rod distally and push the fusion-promoting material out of the exit opening.

In some embodiments, the delivery tube can be filled with fusion-promoting material prior to coupling with the body. The steps of filling of the delivery tube can include coupling a plug over the exit opening of the nozzle. A funnel can be coupled on an end of the delivery tube. The funnel is filled with fusion-promoting material and the fusion-promoting material can be pushed into the delivery tube with a ramrod.

In some embodiments, the method further includes the step of disposing of the delivery tube and the driving rod after injection of the fusion-promoting material.

BRIEF DESCRIPTION OF THE DRAWINGS

These and other features, aspects and advantages of the described embodiments are described with reference to drawings of certain embodiments, which are intended to illustrate, but not to limit. It is to be understood that the attached drawings are for the purpose of illustrating concepts of the described embodiments and may not be to scale.

DETAILED DESCRIPTION

Disclosed herein is a device to aid in the delivery and placement of flowable material to a surgical site such as an intervertebral space. The flowable material can include fusion-promoting material, such as Demineralized Bone Matrix (DBM), allograft, and other bone graft material. In some situations, the flowable material includes medications, saline, water, other fluids, and the like. Although the device is described herein in connection with a spinal surgical procedure, the device can be used in other surgical procedures where delivery of flowable material is desired.

The device, or tool, allows a surgeon to more easily access the surgical site from outside the incision and deliver the fusion-promoting material. In some embodiments, the device allows a surgeon to control the flow rate and dispensing direction of the fusion-promoting material. Additionally disclosed is a device that permits substantially single-handed operation. Such a device frees up an operator's other hand to perform other functions during surgery. In some embodiments, the device can have one or more disposable components that are discarded after use to minimize the potential for cross-contamination and infection. By providing one or more of the preceding advantages, the device described herein improves the ease and speed with which disc replacement, spinal fusion surgery, or other surgery can be completed.

The device will be further described with reference to the drawings, which are intended to be illustrative of certain embodiments of the device, but are not intended to limit the scope of the device. One of skill in the art will recognize that other embodiments of the invention are possible within the scope of the disclosure and no disclaimer of such additional embodiments is intended by referring to the illustrative examples.

Figure 1:
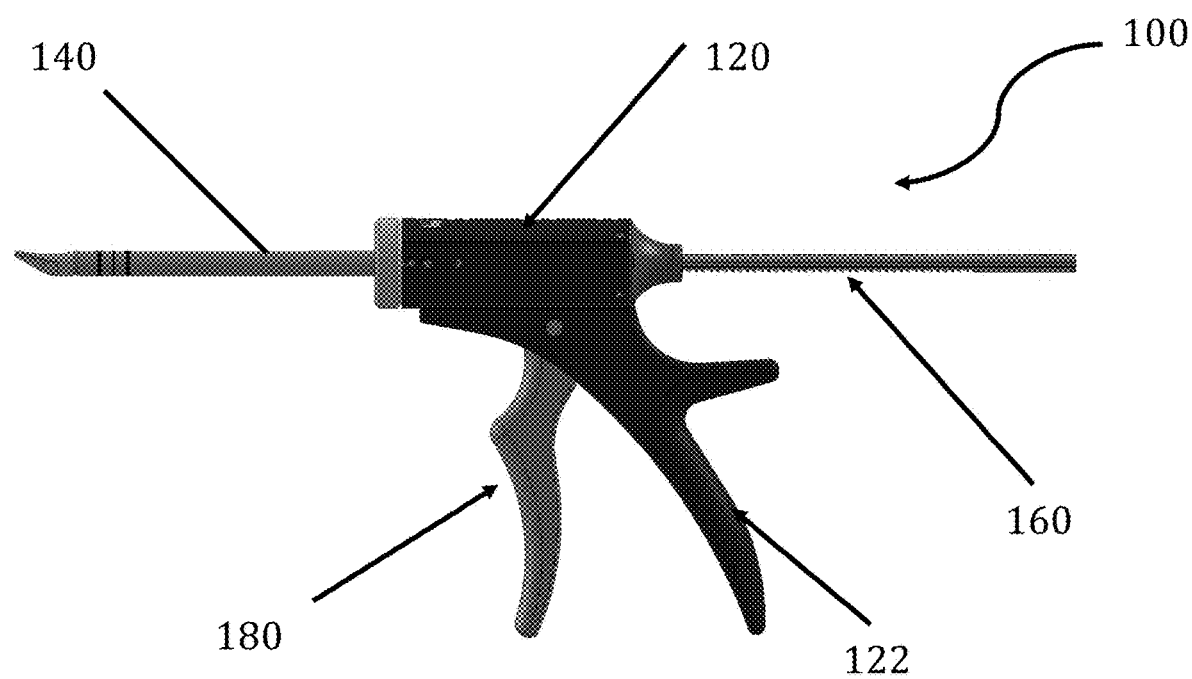
FIG. 1 is a side view of a device for delivering material, in accordance with an embodiment of the present invention.
Figure 2:
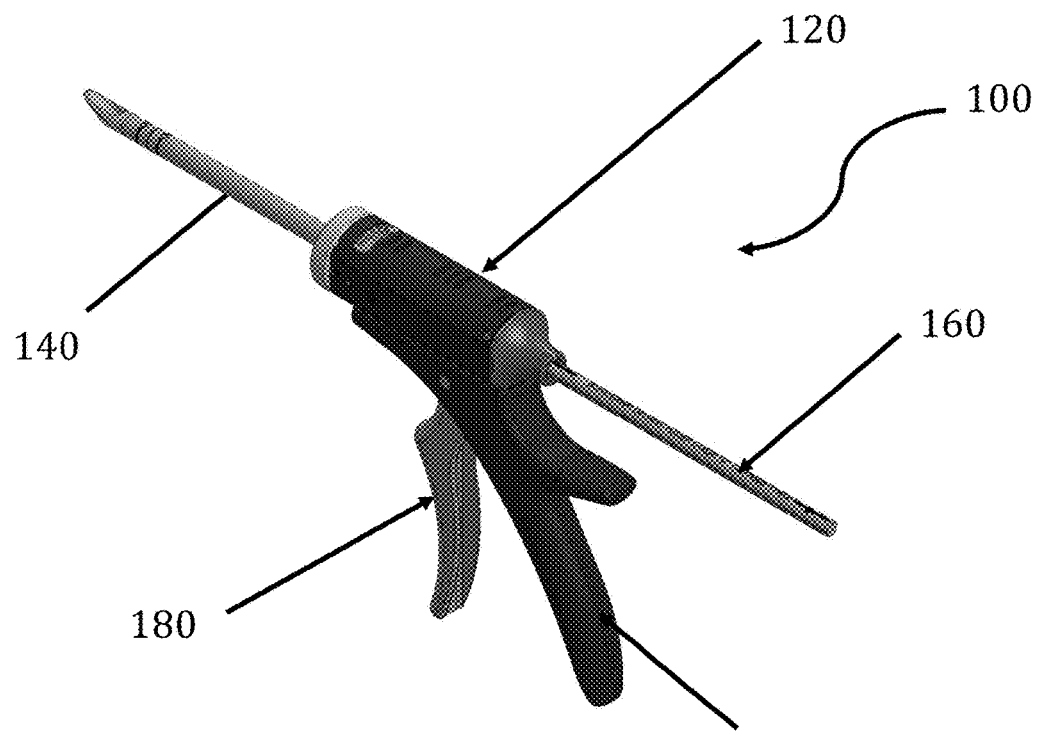
FIG. 2 is a rear perspective view of the device of FIG. 1.
Figure 3:
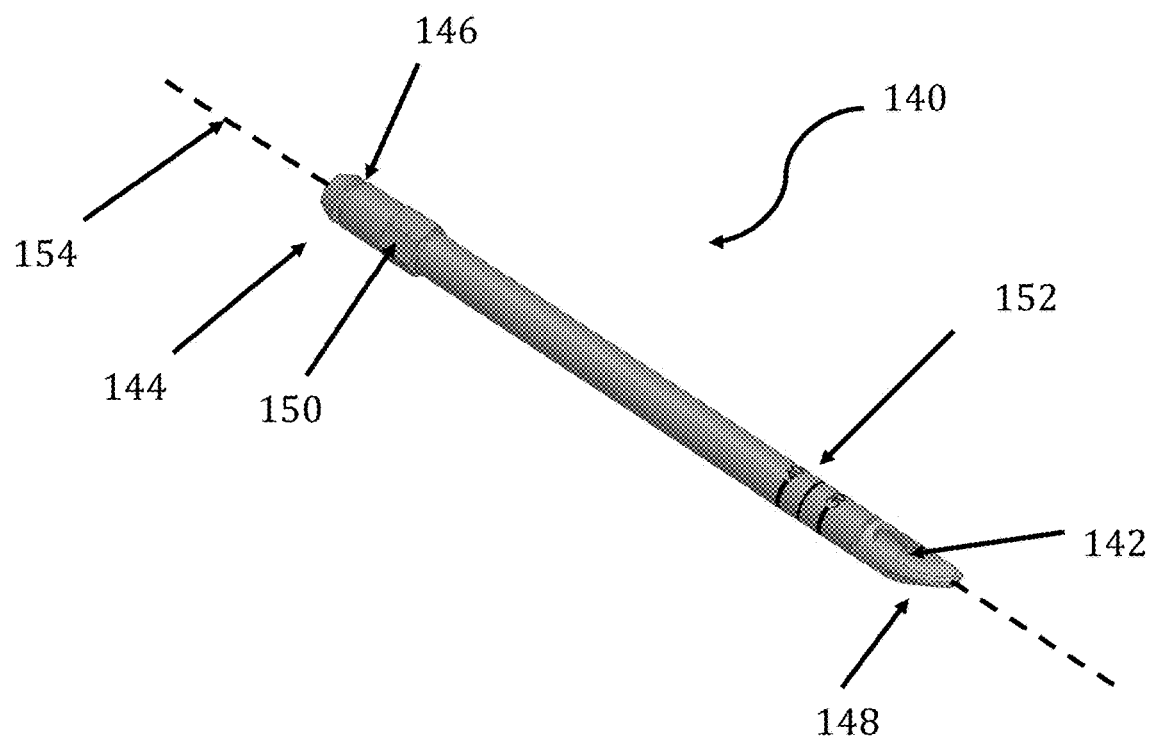
FIG. 3 is a perspective view of a delivery tube of the device of FIG. 1.

FIGS. 1-3 illustrate various external views of an embodiment of the device 100. FIG. 1 is a side view of the device 100 illustrating a body 120, a delivery tube 140 in mechanical communication with the body 120, and a driving rod 160 extending through at least a portion of the body 120 and into the delivery tube 140. FIG. 2 is a perspective view of the device 100. The body 100 can include a handle 122 and a mechanism configured to advance the driving rod 160. In the illustrated embodiment, the mechanism is a lever 180 attached to the handle 122 that can be actuated to move the driving rod 160. In some embodiments, the body 120 does not enclose the driving rod 160 and the driving rod 160 is external to, but in communication with, the body 120.

As used herein, the distal direction of the device 100 is defined as being toward the delivery tube 140 side and the proximal direction is defined as being toward the driving rod 160 side. The bottom of the device 100 is the side with the handle 122 and the top of the device 100 is the side opposite the handle 122.

With continued reference to FIGS. 1-2, the lever 180 is in mechanical communication with the driving rod 160. Movement of the lever 180 toward the handle 122 can urge the driving rod 160 to advance in the distal direction relative to the body 120. The advancement mechanism may operate in any of a plurality of different ways. For example, in the illustrated embodiment the advancement mechanism is a ratcheting drive mechanism within the body 120. The ratcheting drive mechanism can use ratchet teeth to engage the driving rod 160 and advance the driving rod 160 distally when the lever 180 is moved toward the handle 122, as described in further detail below.

The delivery tube 140 can be releasably attached to the distal end of the body 120. FIG. 3 illustrates an embodiment of the delivery tube 140. The delivery tube 140 is an elongate component with a passageway 142 extending along the longitudinal axis 154 of the delivery tube 140. The passageway 142 can transport material from the proximal end 144 to the nozzle 146 where the material is discharged to the surgical site.

The proximal end 144 of the delivery tube 140 can be configured to couple with the distal end of the body 120. In the embodiments illustrated in FIGS. 3-4, the delivery tube 140 includes a hex portion 148 and the body 120 includes an aperture 126 with a complementary hex shape to accept the delivery tube 140. When the delivery tube 140 is inserted into the aperture 126, a locking mechanism can secure the delivery tube 140 to the body 120 to prevent the delivery tube 140 from uncoupling from the aperture 126. The locking mechanism can have any of a plurality of different functional locking designs.

Figure 4:
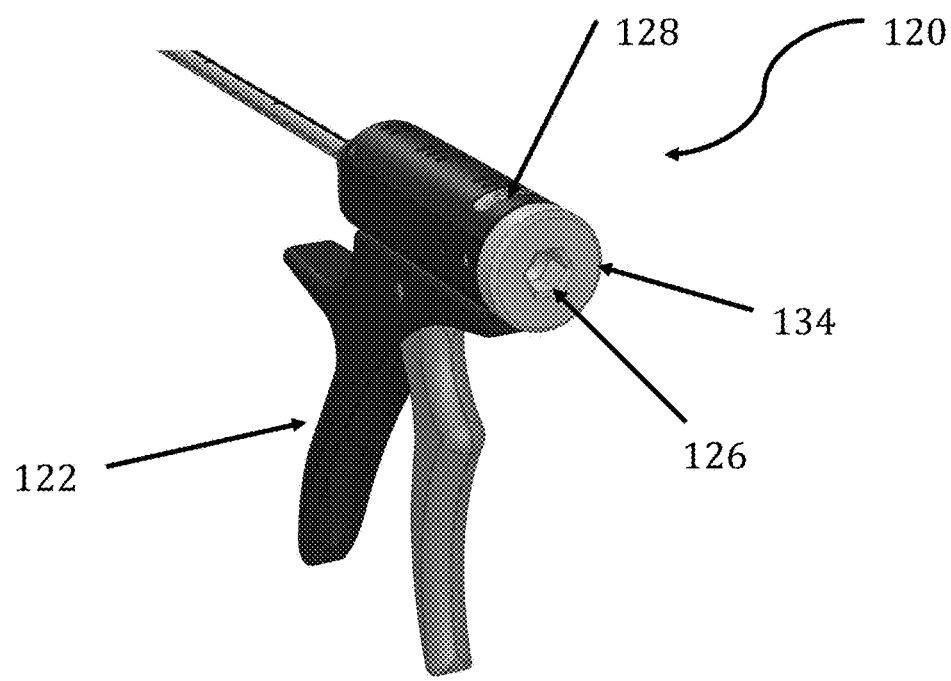
FIG. 4 is a perspective view of a body and a driving rod of the device of FIG. 1.
Figure 5:
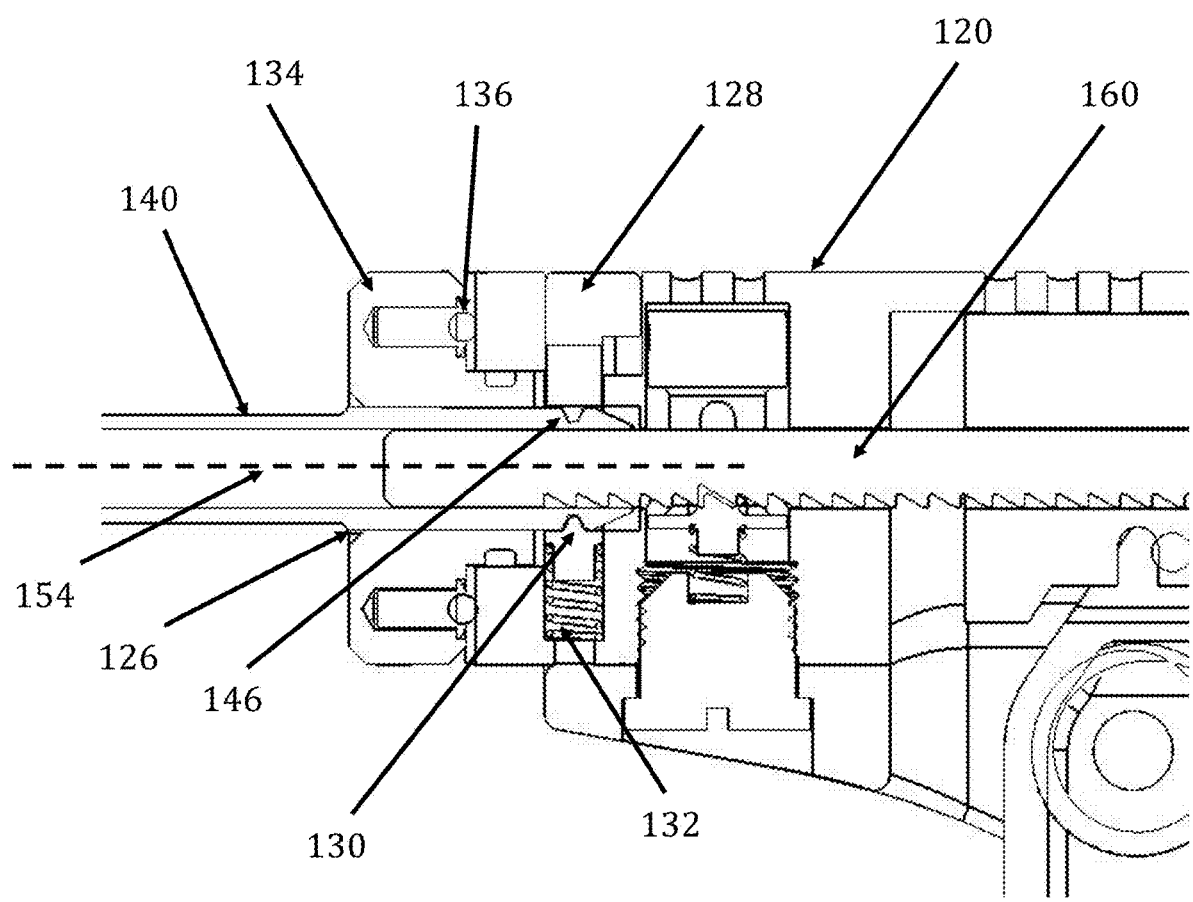
FIG. 5 is a close-up side section view of a portion of the body, delivery tube and driving rod of the device of FIG. 1.

In the illustrated embodiment, the delivery tube 140 has a groove 146, and the body 120 has a sliding sleeve 128 that is configured to engage with the groove 146 on the delivery tube 140 to secure the two components together. With reference to FIGS. 3-5, the groove 146 is an area of the delivery tube 140 with a reduced diameter. The sliding sleeve 128 includes a cutout that can be aligned with the aperture 126 of the body 120 to form an unobstructed passage. The delivery tube 140 can be inserted into the aperture 126 when the cutout of the sliding sleeve 128 is aligned with the aperture 126. The sliding sleeve 128 can then be moved so that a protrusion 130 in the sliding sleeve 128 engages with the groove 146 of the delivery tube 140 to hold the delivery tube 140 on the body 120. The delivery tube 140 is prevented from moving longitudinally and decoupling from the body 120. In some embodiments, the sliding sleeve 128 is a push button mechanism that can be actuated from the outer surface of the body 120. The sliding sleeve 128 can be normally biased in the engage position, such as with a spring 130. When the button is depressed, the sliding sleeve 128 can be in the release position, wherein the protrusion in the sliding sleeve 128 does not obstruct the aperture 126. The delivery tube 140 can be decoupled from the body 120 when the button is depressed.

The distal end of the delivery tube 140 includes a nozzle 148 with an opening to discharge the flowable material. The opening at the nozzle 148 is in fluid communication with an opening at the proximal end 144 of the delivery tube 140 through the passageway 142. In the embodiment illustrated in FIG. 3, the nozzle 148 has an opening that discharges laterally at an angle from the longitudinal axis of the delivery tube; i.e., in a sideways direction from the longitudinal axis. The lateral opening of the nozzle 148 can allow the user to place the delivery tube 140 adjacent a surgical site and discharge the flowable material to efficiently fill in the cavity and help disperse the material throughout the implant site. In some embodiments, the nozzle 148 has an angled inner surface to deflect the flowable material out the lateral opening. The angled nozzle 148 can be particularly useful to reach the space behind an implanted device. The inner surface can have an angle of approximately 30, 45 or 60 degrees from the longitudinal direction. In some embodiments, the angle of the inner surface is at least approximately 15 degrees and/or less than or equal to approximately 90 degrees.

With continued reference to FIG. 3, the delivery tube 140 can have an anti-rotation feature, such as a knob 150 near the proximal end 144. The knob 150 can have a hexagonal shape and is configured to fit in a complementary cavity of the aperture 126. The hexagonal shaped coupling allows the delivery tube 140 to be secured to the body 120 in 60 degree increments so that the nozzle orientation can be turned in several directions. In some embodiments, the knob 150 can have other shapes, such as triangular, square, octagonal, star, oval or any other non-circular shape. The orientation of the nozzle can be rotated in any increments depending on the shape of the knob and aperture, such as 15 degrees, 30 degrees, 45 degrees, 90 degrees, 120 degrees or 180 degrees. In some embodiments, the orientation of the nozzle is adjustable in increments from at least approximately 1 degree and/or less than or equal to approximately 180 degrees.

In some embodiments, the orientation of the nozzle can be adjusted without removing and reinserting the delivery tube 140 in a different orientation. The aperture 126 and knob 150 can have any of a plurality of different rotational mechanisms. For example, the illustrated embodiment shows the body 120 with a rotatable collar 134. The collar 134 includes the aperture 126 that is configured to couple with the knob 150. The collar 134 can be rotated, which in turn rotates the delivery tube 140 about its longitudinal axis 154 to orient the nozzle in the desired direction. In the illustrated embodiment, the collar 134 has a plunger 136 with a ball that is configured to engage detents on the body 120. The detents can be arranged in a circular configuration. The number and spacing between detents can be determined depending on the desired rotational orientations for the nozzle. As the number of detents increases, the delivery tube 140 can be set to finer increments of rotational orientations.

Other rotational mechanisms are also envisaged for the device 100. For example, the knob 150 can have a ball plunger and the aperture 126 can have detents around the inner perimeter where the ball protrusion can engage in order to hold the delivery tube 140 in discreet rotational orientations. In another example, the collar 134 can have a plurality of teeth and the body 120 can have a tab that engages the teeth to rotationally lock the collar. The tab can be released by depressing a button to release the tab from the teeth. In some embodiments, the rotational orientation of collar 134 is infinitely adjustable and can be rotated to any angle, such as a collar with a friction locking mechanism that clamps on the collar to secure it in position.

In some embodiments, the delivery tube 140 is rigid. The delivery tube 140 may not bend or only have minimal bending so that the nozzle 148 can be pushed to the surgical site through obstacles. In other embodiments, the delivery tube 140 is flexible and can bend along its longitudinal axis 154 to help route the delivery tube 140 around obstacles in the patient's anatomy to the surgical site. In embodiments with a flexible delivery tube, the delivery tube 140 is preferably sufficiently rigid so that the passageway 142 does not collapse or kink.

The delivery tube 140, or portions thereof, can be made of any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the above materials. The delivery tube 140 can be made of multiple materials in combination. For example, the proximal portion can be made of a metal and the nozzle can be made of a polymer. The delivery tube 140 is preferably made of a biocompatible material.

With continued reference to FIG. 3, the delivery tube 140 can have indications 152 along the length of the tube. The indications 152 can be markings that display the position from the distal tip of the delivery tube 140 to inform the user of the depth of insertion into the patient's body. In some embodiments, the indications 152 include distance measurements, such as in inches, millimeters, centimeters, and the like. In some embodiments, the indications 152 show relative depth, such as with different colored indications, lines of increasing thickness, increasing sequential numbers, or any of a plurality of other indications that show increasing depth. The indications 152 can be placed along the entire length of the delivery tube 140 or only a portion of the length of the delivery tube 140.

Figure 6:
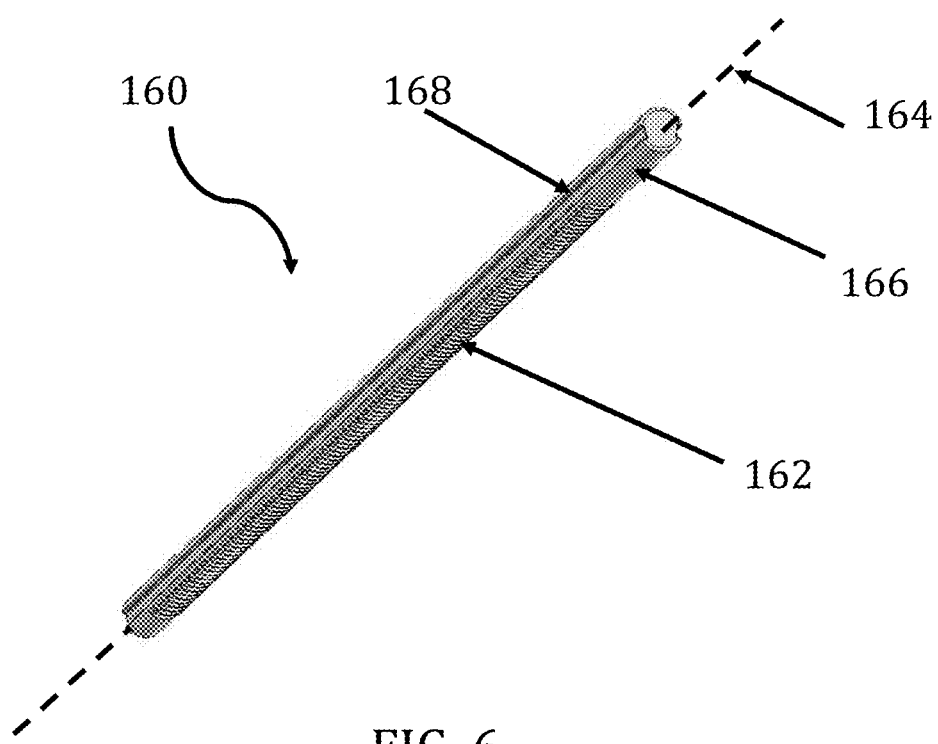
FIG. 6 is a perspective view of the driving rod of FIG. 1.

In the embodiment illustrated in FIG. 6, the driving rod 160 is an elongate member having a longitudinal axis 164 and a surface 166 with a plurality of ratchet teeth 162 on at least a portion of the surface 166. The driving rod 160 is configured to insert into a hole 124 disposed on the proximal end of the body 120. In other embodiments, the driving rod 160 is inserted from a distal end of the body 120, or from the top side of the body 120, or any other side of the body that provides access into the body. The driving rod 160 can extend through the body 120 and the driving rod 160 can be advanced in the distal direction by an advancement mechanism. The advancement mechanism can be in mechanical communication with the ratchet teeth 162 to move the driving rod 160. The driving rod 160 is configured to fit into the passageway 142 of the delivery tube 140 to push the flowable material out the nozzle 146 of the delivery tube 140.

Figure 7:
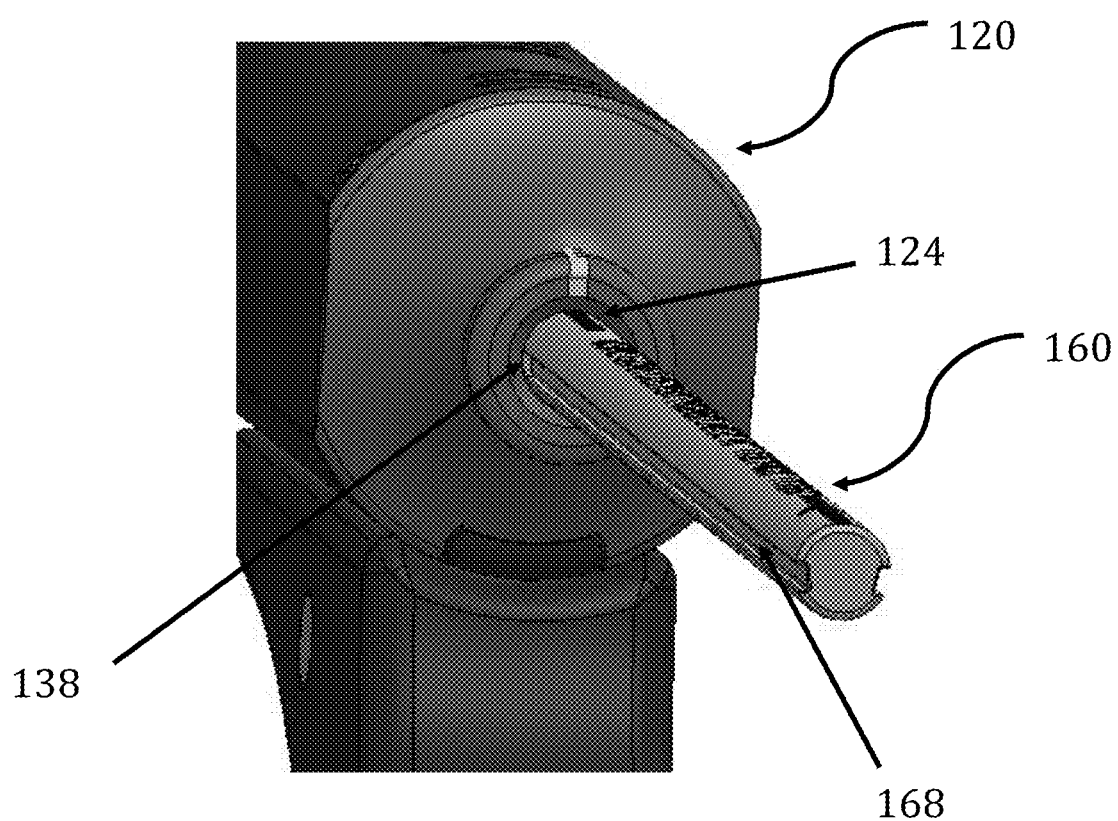
FIG. 7 is a close-up rear perspective view of the driving rod and body of FIG. 1.

FIG. 7 illustrates an embodiment of the proximal end of the body 120 with the hole 124 through which the driving rod 160 is inserted. The hole 124 can have a shape and size that matches and/or is complementary to the shape and size of the driving rod 160. The driving rod 160 can be inserted into the hole 124 with the ratchet teeth 162 facing downward (i.e. toward the handle) to engage with the advancement mechanism. In some embodiments, the rotational orientation of the driving rod 160 when inserting into the hole 124 is set by aligning an indicator (e.g., a line marking) on the driving rod 160 with a second indicator on the body 120.

The driving rod 160 and hole 124 can be configured so that the driving rod 160 can only be inserted in one or more desired rotational configurations. In some embodiments, the hole 124 has at least one tab 138 and the driving rod 160 has a complementary channel 168 for inserting the driving rod 160 in the desired orientation into the hole 124. The driving rod 160 can be inserted into the hole 124 only when the tab 138 is aligned with the channel 168 to ensure that the driving rod 160 is in the desired orientation. In the embodiment illustrated in FIG. 7, the hole 124 has two tabs 138 and the driving rod 160 has two channels 168. The tabs 138 in the illustrated embodiment are not 180 degrees apart such that the driving rod 160 can be inserted into the hole 124 in only one orientation. In a different example, the hole can have two tabs that are 180 degrees apart and the driving rod can have two channels 180 degrees apart so that the driving rod can be inserted in either of two orientations. In another example, the hole can have one tab and the driving rod can have a plurality of channels, such as six channels equally distanced around the driving rod, so that the driving rod can be inserted in six different orientations that are 60 degrees apart. In embodiments where the driving rod can be inserted in more than one orientation, the driving rod can have ratchet teeth on several surfaces so that the ratchet teeth can engage the advancement mechanism in all the different orientations.

In some embodiments, the driving rod 160 is locked rotationally so that the driving rod 160 cannot rotate once it is inserted in the body 120. For example, the tab 138 and channel 168 engagement discussed above can prevent the driving rod 160 from rotating in the hole 124. The rotationally locked configuration can help prevent disengagement of the advancement mechanism. For example, as discussed herein, the driving rod 160 can have ratchet teeth 162 that face downward in order to engage with ratchet pawls. The rotationally locked configuration can ensure that the ratchet teeth 162 stay engaged with the ratchet pawls during operation of the device.

Figure 8:
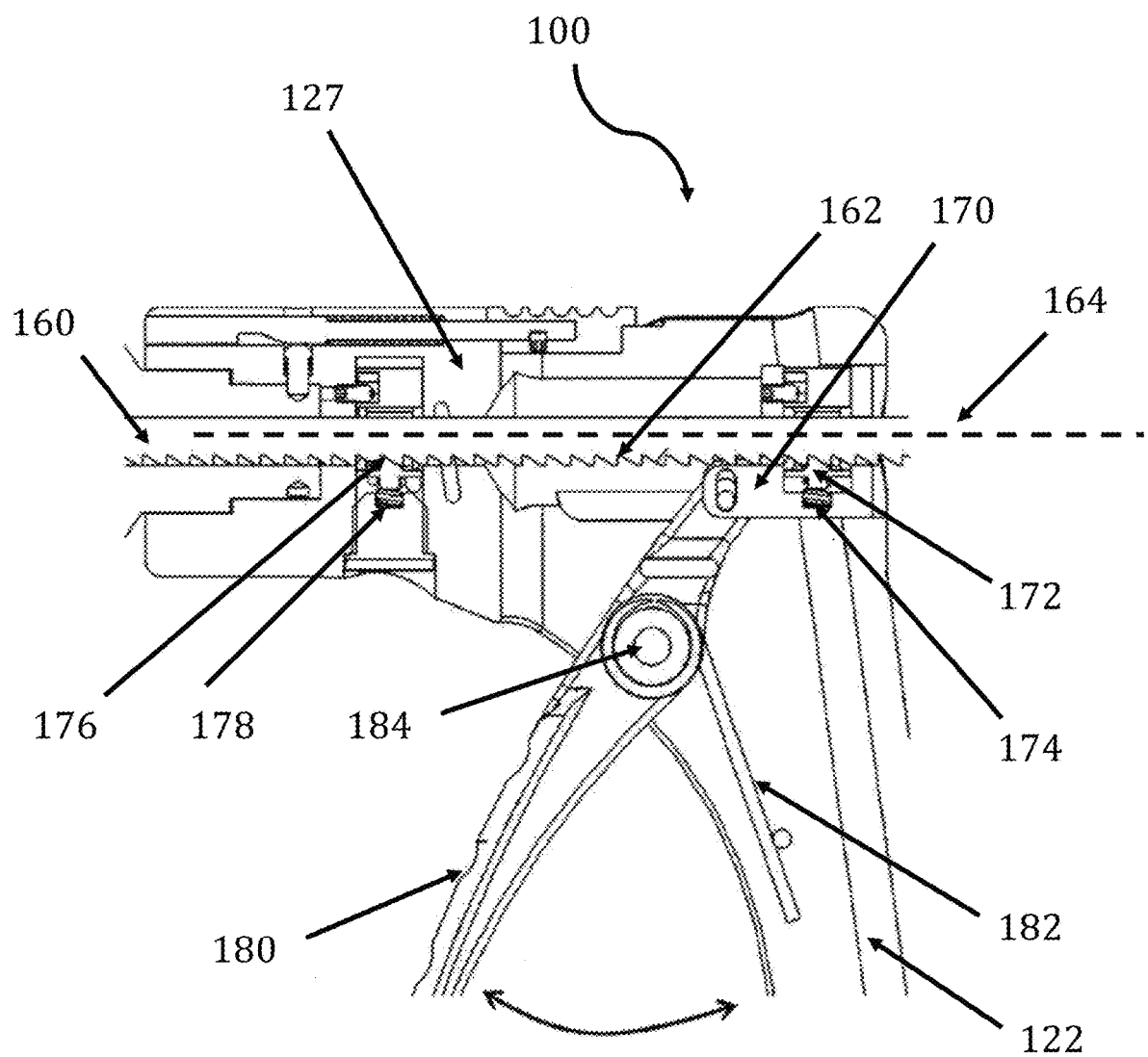
FIG. 8 is a side section view of the body of FIG. 1 illustrating the advancement mechanism.

FIG. 8 is a cutaway side view of an embodiment of the device 100 showing the internal cavity 127 of the body 120. In the cavity 127, the ratchet teeth 162 of the driving rod 160 can engage with an advancement mechanism 170 of the body 120. Further shown is a first ratchet pawl 172 and a first pawl spring 174 which work together with the lever 180, lever spring 182 and lever pivot 184 to drive the driving rod 160 distally when the lever 180 is moved toward the handle 122 (i.e. toward a second position from a first position, shown by the double-headed arrow of FIG. 8). When an operator grips the handle 122 and the lever 180 in one hand and pulls the lever 180 proximally toward the handle 122, the lever 180 moves the first ratchet pawl 172 distally by pivoting about the lever pivot 184. Since the first ratchet pawl 172 is engaged against the ratchet teeth 162 of the driving rod 160, the distal motion of the ratchet pawl 172 drives the driving rod 160 distally. Also depicted in this view are a second ratchet pawl 176 and a second pawl spring 178. The second ratchet spring 178 allows the second ratchet pawl 176 to move away from the driving rod 160 as each angled ratchet tooth 162 advances distally. Once each tooth 162 passes the second pawl 176, the pawl spring 178 pushes the second pawl 176 back toward the driving rod 160, to engage the next ratchet tooth 162 along the driving rod 160. Thus the second ratchet pawl 176 allows distal motion of the driving rod 160 and prevents proximal motion of the driving rod 160. As the lever 180 is pulled again or farther toward the handle 122, further distal motion is imparted to the driving rod 160.

Thus, the second ratchet pawl 176 and the second pawl spring 178 cooperate to restrict or oppose proximal motion of the driving rod 160 as the lever 180 is reset away from the handle 122. In the illustrated embodiment, the lever 180 has a spring 182 that biases the lever 180 toward the first position. Once the operator releases the force on the lever 180, the lever spring 182 can move the lever 180 away from the handle 122 toward its original position. As this occurs, the first ratchet pawl 172 and first pawl spring 174, coupled to the lever 180, are also returned toward their original positions prior to the operator pulling the lever 180 proximally. This occurs with no distal or proximal motion of the driving rod 160 since the first pawl spring 174 allows the first ratchet pawl 172 to move away and toward the driving rod 160 along the ratchet teeth 162 of the rod 160 as the first ratchet pawl 172 moves along the teeth 162 proximally. The second ratchet pawl 176, engaged against the ratchet teeth 162, opposes proximal motion of the rod 160 during this action. In embodiments where a gripping or other type of driving mechanism is used, the second ratcheting pawl 176 and spring 178 may be used to provide similar restricted proximal motion where the driving rod 160 comprises some ratchet teeth 162 on at least a portion of the rod 160 which can cooperate with the second ratchet pawl 176 and spring 178.

It is to be understood that the lever spring 182 may be eliminated in some embodiments and still provide substantially single-handed operation. In such cases, the lever 180 can be moved toward the first position manually. This can be facilitated by including a closed handle (loop) similar to those common on scissors and forceps at the lower end of the lever 180, through which an operator may place her fingers and by means of which an operator can impart force to the lever 180 in either the direction away from or toward the handle 122 with a single hand.

In another embodiment, the device comprises a holding means wherein a second ratchet pawl and second ratchet spring are not present. The holding means instead may comprise, for example, a pneumatic grip, a hook, a latch, a grabbing device, the gripping mechanism described further herein, manually holding the driving rod in its distal position, or another mechanical means of restricting proximal motion.

In other embodiments, the device comprises a driving means comprising a first ratchet pawl and a spring that engages a thread which winds around the driving rod. Ratchet teeth may be unnecessary in this embodiment. The lever may instead drive the driving rod distally by engaging the threads in the same ratcheting manner described herein, and retraction may be achieved by rotating the driving rod such that the rod moves proximally with the ratchet pawls engaged against the threads of the driving rod.

In other embodiments, the device comprises a driving mechanism comprising for example, a pneumatic grip, a hook, a latch, a grabbing device, the gripping mechanism (described further below), an element adapted and configured for manually pushing the driving rod distally, or another mechanical means of moving the driving rod distally to push the flowable material through the delivery tube. These and similar embodiments will be apparent to the person skilled in the art upon consideration of alternative embodiments described herein.

As illustrated in the embodiment of FIG. 8, in operation a first ratchet pawl 172 engages the ratchet teeth 162 of the driving rod 160 and a first pawl spring 174 opposes motion of the first ratchet pawl 172 away from the driving rod 160 (downward, in the depicted embodiment, although, it could be in any direction away from the driving rod 160). Also shown is a second ratchet pawl 176. A second pawl spring 178 opposes motion of the second pawl 176 away from the driving rod 160 (downward, in this case, although it could be in any direction away from the driving rod 160). Further depicted is the lever pivot 184 about which the lever 180 pivots to drive the driving rod 160 distally by engaging and moving the ratchet teeth 162 distally when the lever 180 is moved toward the handle 122. Also depicted is the lever spring 182, which opposes lever 180 movement toward the handle 122, and which is capable of moving the lever 180 away from the handle 122 when the lever 180 is released.

Figure 9:
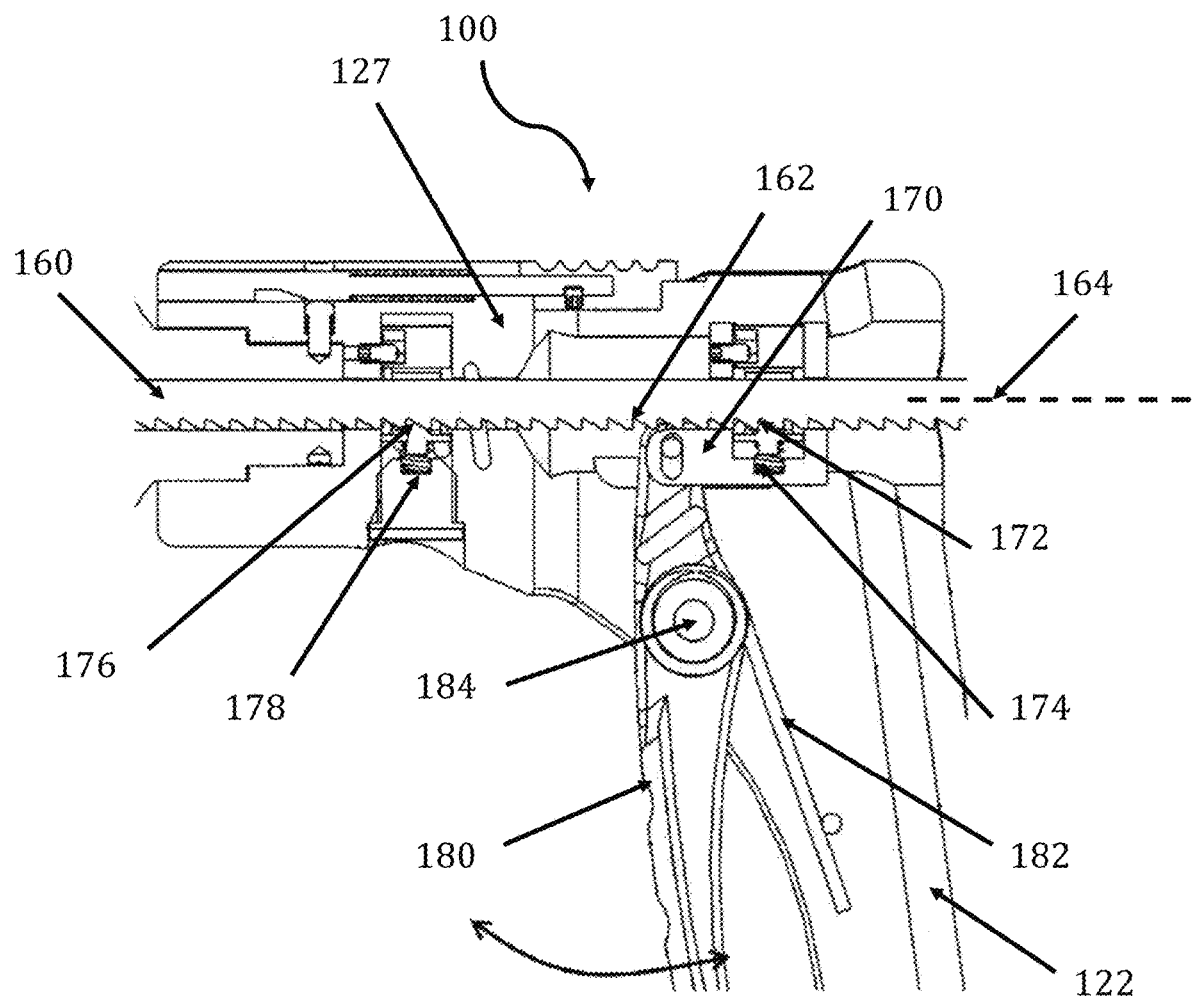
FIG. 9 is another side section view of the body of FIG. 1 with the trigger actuated.

FIG. 9 is a cutaway side view of an embodiment of the device 100 showing the cavity 127 of the body 120. In the illustrated embodiment, the ratchet teeth 162 are engaged by the advancement mechanism 170, wherein the lever 180 is in a second position toward the handle 122. The advancement mechanism 170, the first ratchet pawl 172, and the driving rod 160 are shown as they appear when the lever 180 is moved toward the handle 122. As can be seen, movement of the lever 180 toward the handle 122 causes the first ratchet pawl 172, and the driving rod 160 to move distally, through engagement of the ratchet pawl 172 with the ratchet teeth 162 of the driving rod 160.

In some embodiments, the device 100 is adapted for single-handed use. It is to be understood in regards to the phrase "single-handed," the functions of holding the device in place and advancing the driving rod 160 may, in most instances, be performed with a single hand. However, it is also noted that in some cases, depending upon operator preference and the vagaries of patient physiology, two hands may be used, e.g. to impart greater force to the lever 180, without departing from the spirit and scope of the disclosure. The phrase "single-handed" thus distinguishes embodiments of the present device over other fluid delivery devices in which the device is held in place with one hand and the material is delivered by pushing, twisting or striking an injection arm. In preferred embodiments, the device of the present disclosure also permits the operator to hold the device in place and impart force for insertion with a single hand. In addition to the aforementioned advantages, single-handed use is amenable to less invasive surgery than two-handed use.

In some embodiments, the ratchet teeth 162 extend along the driving rod 160 a length sufficient to allow the driving rod 160 to advance to the nozzle 148 of the delivery tube 140. For example, the ratchet teeth 162 can extend along the length of the driving rod 160 for between about 6 and about 10 inches, for about 8 inches, for about 12 inches, for about 16 inches, for at least 3 inches, or for the entire length of the rod. In referring to the ratchet teeth length along the rod, "about" refers to variations of 0.5 inches to 1 inch, or of 1 inch to 2 inches.

In some embodiments, the device is configured so that the driving rod 160 can only be advanced in the one direction. For example, the advancement mechanism 170 may be configured to move the driving rod 160 distally but not proximally. Moving the driving rod 160 only in the distal direction can help prevent contamination of the body 120, which can be difficult to clean and sterilize, particularly the internal mechanisms of the body 120. Also, in procedures where more than one delivery tube 140 and/or driving rod 160 are used, the body 120 can be interchangeably used with several delivery tubes and driving rods without cross-contamination of materials.

Some embodiments of the device are adapted and configured to allow retraction of the driving rod in the proximal direction. This may be achieved in any of a plurality of different ways. In some embodiments, the surface of the driving rod 160 comprises an area that is substantially free of ratchet teeth on a contiguous longitudinal surface of the driving rod, and the driving rod 160 is movable proximally relative to the body 120 upon rotation of the driving rod 160 about its longitudinal axis 164 such that the ratchet pawls 172, 176 are no longer engaged with the ratchet teeth 162 and are instead in contact with the contiguous longitudinal surface that is free of ratchet teeth 162. In some embodiments, the ratchet teeth 162 disengage from first and second ratchet pawls 172, 176 upon rotation of the driving rod 160 about its longitudinal axis 164. In some embodiments, the driving rod 160 comprises a proximal end having a handle to rotate the driving rod.

Although this retraction is preferably carried out by the operator holding the handle 122 in one hand and turning the driving rod 160 with the other, this action is not to be interpreted as derogating in any way single-handed operation of the device 100, as single-handed operation generally refers to simultaneously holding the handle 122 and imparting drive force to the lever 180 with a single hand, and that only in most cases. As the driving rod 160 may be easily disengaged from the ratchet pawls 172, 176 with, for example, a single 180 degree twist about the axis 164, it is considered that the present disclosure provides for easy and fast retraction of the driving rod 160.

In other embodiments, the driving rod may comprise a threading around the driving rod instead of ratchet teeth, wherein the ratchet pawls 172, 176 may engage the threads instead of ratchet teeth. The driving rod 160 can be retracted by turning the driving rod 160 about the longitudinal axis 164 to unscrew the threads. Other embodiments may comprise combinations of threads, ratchet teeth, and/or a substantially smooth area along the driving rod surface, and a combination of ratcheting and gripping elements to provide the controlled distal and proximal movement of the driving rod.

If needed or desired, retraction of the driving rod 160 using the features and methods described herein may also allow return or suction of the flowable material. When the driving rod 160 is moved in the proximal direction in the passageway 142 of the delivery tube 140, the vacuum created by the retracted driving rod 160 can cause the flowable material to be sucked back into the delivery tube 140. This feature can be used to collect excess flowable material that was dispensed, collect flowable material for repositioning, or collect other fluids in the surgical site for disposal. For example, blood in the surgical site can be collected in the delivery tube 140 by retracting the driving rod 160 to suck up the blood.

Figure 10:
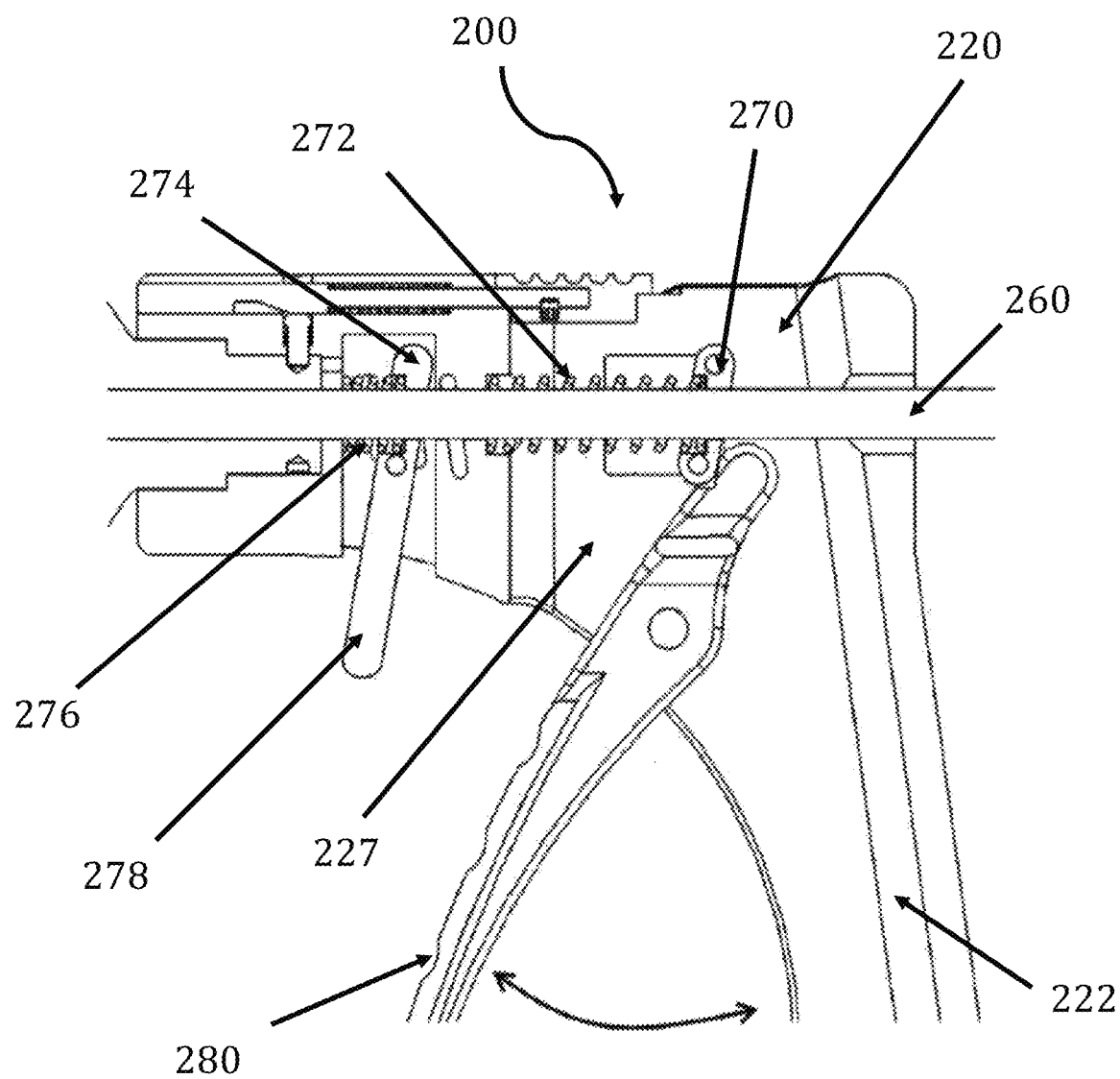
FIG. 10 is a side section view of a body, in accordance with another embodiment of the present invention.

FIG. 10 is a cutaway side view illustrating a non-ratcheting embodiment of a device 200. The device 200 can have a body 220 with an internal cavity 227 housing two gripping elements 270, 274, wherein the first gripping element 270 is adapted and configured to grip and push the driving rod 260 distally when the lever 280 is moved toward the handle 222. The second gripping element 274 allows distal movement of the driving rod 260, but opposes proximal motion of the driving rod 260 when the lever 280 is released and allowed to move away from the handle 222, for example, to its original resting (first) position. The first gripping element 270 also releases its grip on the driving rod 260 when the lever 280 is moved away from the handle 222, for example, to its original resting position. The first gripping spring 272 moves the first gripping element 270 proximally when the lever 280 is released. The first gripping element 270 is adapted and configured to only grip the driving rod 260 upon distal motion of the driving rod 260. Similarly, the second gripping element 274 is adapted and configured to only grip the driving rod 260 upon proximal motion of the driving rod 260.

With continued reference to FIG. 10, the first gripping spring 272 can bias the first gripping element 270 in the proximal direction. When an operator moves the lever 280 toward the handle 222, the lever 280 can push the lower part of the first gripping element 270 distally, which tilts the first gripping element 270. The tilt can enable the first gripping element 270 to grip the driving rod 260 and move it distally. When the lever 280 moves away from the handle 222, the first gripping element 270 moves proximally to return to its proximal-most position. The force from the first gripping spring 272 can make the first gripping element 270 less tilted to enable the first gripping element 270 to slide over the driving rod 260 without gripping the rod. Movement of the lever 280 away from the handle 222 may be manually forced, or may be the result of a lever spring within the handle 222 that is coupled to the lever pivot. In some embodiments, the first gripping spring 272 pushes the lever 280 away from the handle 222.

A second gripping element 274 is normally biased in a tilted position by a second gripping spring 276. When the driving rod 260 moves in the distal direction, the second gripping element 274 becomes less tilted and allows the driving rod 260 to slide through the second gripping element 274. However, the second gripping element 274 grips the driving rod 260 and prevents the driving rod 260 from moving proximally when the first gripping element 270 is moved proximally. A gripping release lever 278 can be actuated to make the second gripping element 274 less tilted, which releases the second gripping element 274 and allows the driving rod 260 to be retracted.

In some embodiments of the device comprises a gripping element and a ratcheting drive mechanism as described previously. Some embodiments comprise other means for moving the driving rod distally. Other mechanical mechanisms may be capable of allowing unidirectional movement, along with having a release mechanism for reversing such unidirectional movement.

Figure 11:
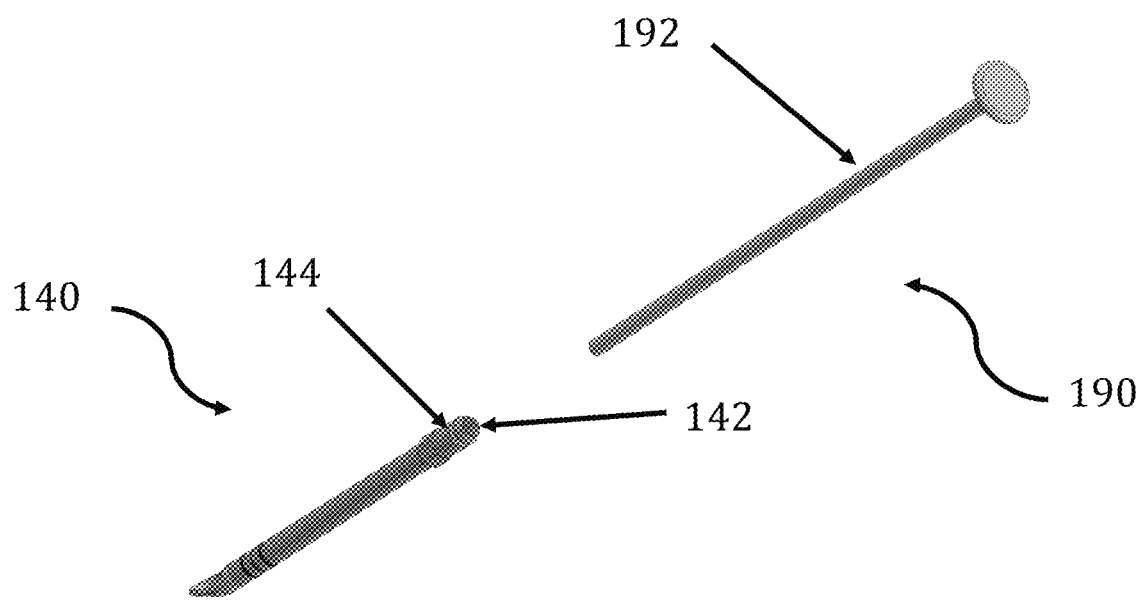
FIG. 11 is a perspective view of a delivery tube and a ramrod, in accordance with an embodiment of the present invention.

In some embodiments, the delivery tube 140 is preloaded with flowable material prior to being mounted to the body 120. The flowable material can be viscous and it may be difficult to pack the material into the passageway 142 of the delivery tube 140. Preloading the delivery tube 140 while it is disconnected from the body 120 can make the packing of the flowable material easier and faster. As illustrated in FIG. 11, a ramrod 190 can be used to pack the flowable material into the delivery tube 140. The ramrod 190 can have an elongate shaft 192 that is configured to slide within the passageway 142 of the delivery tube 140. For example, the passageway 142 can have a circular cross-sectional shape and the ramrod 190 can have a cylindrically shaped shaft, wherein the passageway 142 and the ramrod 190 are substantially the same diameter. In other embodiments, the passageway can have a cross-sectional shape that is square, star, polygon, oval, or any other shape. The ramrod 190 has a shaft with a shape that is complementary to the shape of the passageway.

Figure 12:
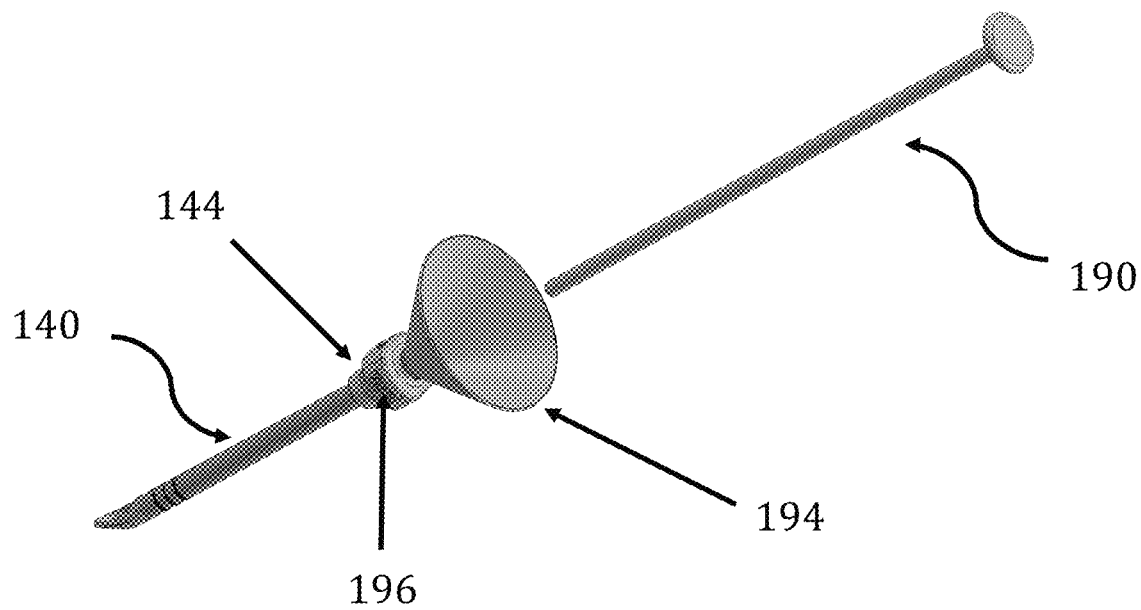
FIG. 12 is a perspective view of a delivery tube, a funnel and a ramrod, in accordance with an embodiment of the present invention.

The flowable material can be inserted in the passageway 142 of the delivery tube 140 and the ramrod 190 can be used to push and compact the flowable material in the passageway 142. As discussed previously, the cross-section of the shaft 192 of the ramrod 190 is preferably substantially the same size and shape as the cross-section of the passageway 142 to effectively and efficiently move the flowable material through the passageway 142 without leakage around the shaft 192. A funnel 194 can be used to help insert the flowable material into the passageway 142, as illustrated in FIG. 12. The funnel 194 can couple to the proximal end 144 of the delivery tube 140 such that the inside of the funnel is in fluid communication with the passageway 142.

The funnel 194 can be coupled to the delivery tube 140 through any of a plurality of different releasable connections, such as for example a compression fitting, interference coupling, threaded connection, or any other functional coupler. In some embodiments, the funnel 194 has a funnel sleeve 196 that is configured to engage with the groove 146 on the delivery tube 140 to secure the two components together. As discussed above, the groove 146 is an area of the delivery tube 140 with a reduced diameter. The funnel sleeve 196 includes a cutout that can be aligned with the drain tube of the funnel 194 to form an unobstructed passage. The funnel 194 can be coupled over the delivery tube 140 when the cutout of the funnel sleeve 196 is aligned with the drain tube. The funnel sleeve 196 can then be moved so that a protrusion in the funnel sleeve 196 engages with the groove 146 of the delivery tube 140 to hold the funnel 194 on the delivery tube 140, similar to described above for the connection between the body 120 and the delivery tube 140. In some embodiments, the funnel sleeve 196 is a push button mechanism that can be actuated from the outer surface of the funnel 194. The funnel sleeve 196 can be normally biased in the engage position, such as with a spring. When the button is depressed, the funnel sleeve 196 can be in the release position, wherein the protrusion in the funnel sleeve 196 does not obstruct the drain tube. The funnel 194 can be decoupled from the delivery tube 140 when the button is depressed.

Figure 13:
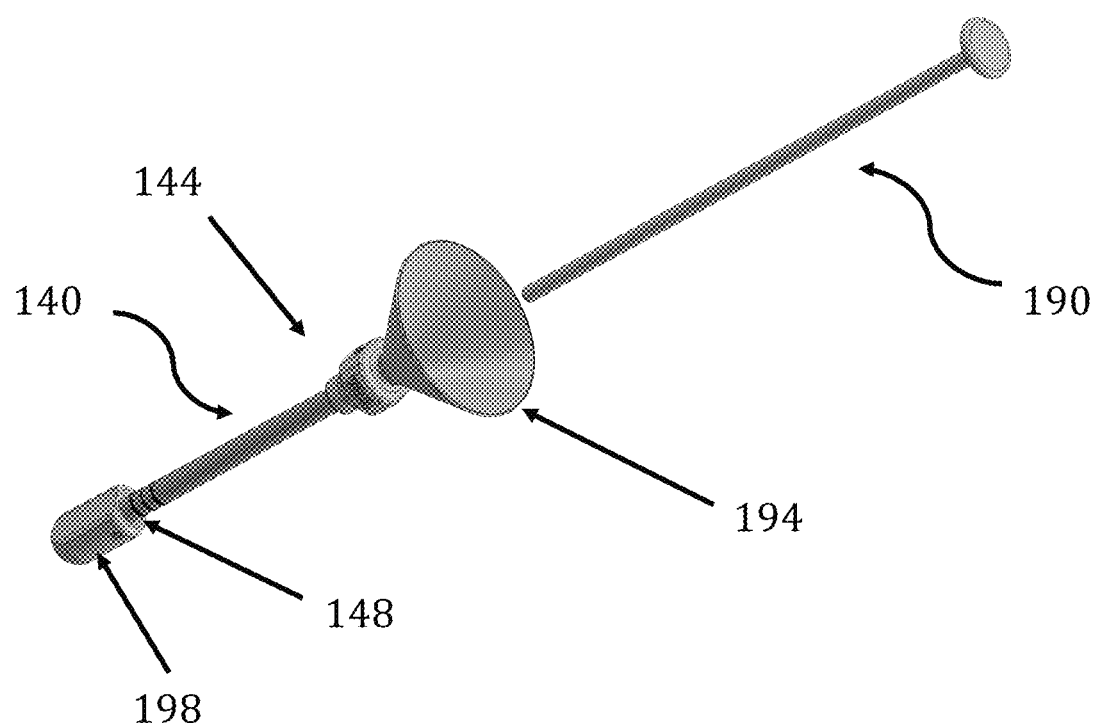
FIG. 13 is a perspective view of a delivery tube, a funnel, a plug and a ramrod, in accordance with an embodiment of the present invention.

With reference to FIG. 13, a plug 198 can be placed over the nozzle 148 of the delivery tube 140 to prevent the flowable material from unintentionally exiting out the nozzle 148 as the delivery tube 140 is filled from the proximal end 144. In some embodiments, the plug 198 has a cavity, which accepts the nozzle 148 to block the exit opening of the nozzle 148. The plug 198 can be coupled to the delivery tube 140 through any of a plurality of different releasable connections, such as for example a compression fitting, interference coupling, threaded connection, or any other functional coupler. In the illustrated embodiment, the plug 198 includes setscrews that are fastened against the nozzle 148 to fix the plug 198 onto the delivery tube 140. The ramrod 190 can be used to pack the flowable material in the delivery tube 140 in preparation for dispensing in the surgical site. The delivery tube 140 can be packed either with or without the plug 198 attached to the distal end.

Figure 14:
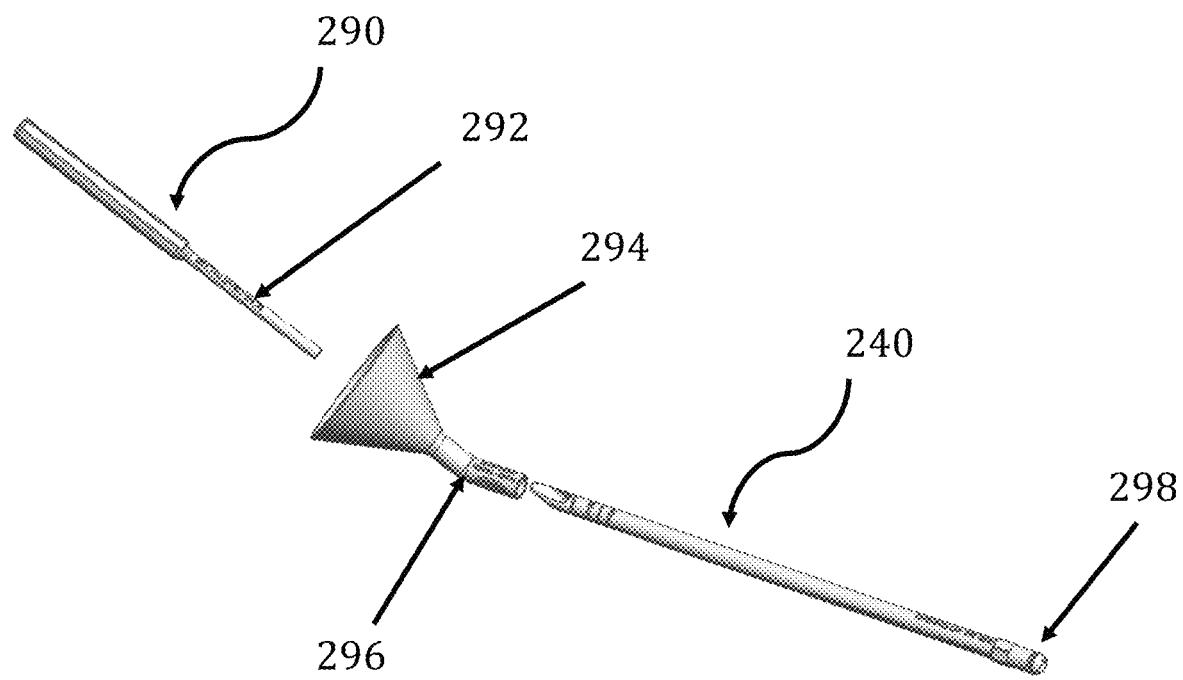
FIG. 14 is a perspective view of a delivery tube, a funnel, a plug and a ramrod, in accordance with another embodiment of the present invention.

As illustrated in FIG. 14, a funnel 294 can be coupled to a distal end of the delivery tube 240 through any of a plurality of different releasable connections, such as for example a compression fitting, interference coupling, threaded connection, or any other functional coupler. Coupling the funnel 294 on the distal end of the delivery tube 240 can help to reach and fill the distal portion of the delivery tube 240 with flowable material, particularly when the flowable material is viscous. In some embodiments, a plug 298 is placed over the proximal end of the delivery tube 240 to prevent the flowable material from unintentionally exiting out the proximal end as the delivery tube 140 is filled from the distal end. The plug 298 can have a cavity that accepts the proximal end of the delivery tube 240 to block the opening of the passageway. The plug 298 can be coupled to the delivery tube 240 through any of a plurality of different releasable connections, such as for example a compression fitting, interference coupling, threaded connection, or any other functional coupler. In some embodiments, the plug 298 includes setscrews that are fastened against the delivery tube 240. In other embodiments, the plug 298 has protrusions on the inner surface that fits into a groove on a surface of the delivery tube 140.

Figure 15:
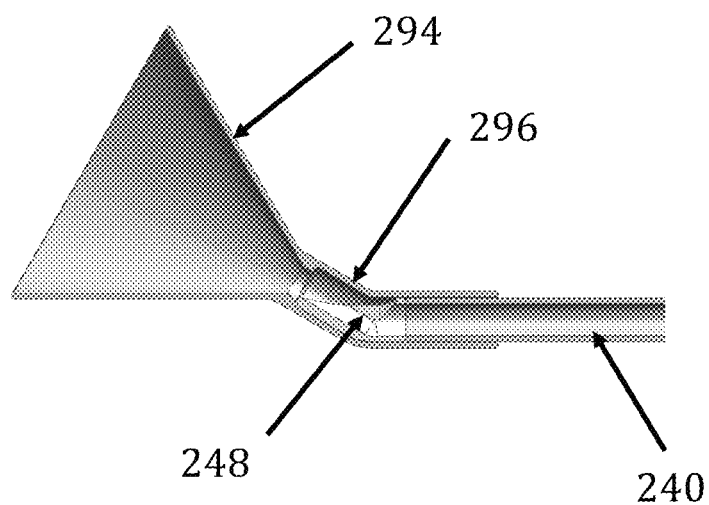
FIG. 15 is a close-up side section view of the delivery tube and the funnel of FIG. 14.

The funnel 294 can fit over the nozzle 248 and is configured to direct the flowable material into the opening in the nozzle 248. In the illustrated embodiment of FIG. 15, the funnel stem 296 has a bent shape. The angle of the bend can generally coincide with the angled inner surface of the nozzle, as discussed above. As illustrated in FIG. 15, a first portion of the funnel stem 296 is configured to fit over the distal portion of the delivery tube 240. A second portion of the funnel stem 296 is configured to direct flowable material into the opening in the nozzle 248.

The ramrod 290 can be used to push the flowable material into the passageway of the delivery tube 240 before dispensing in the surgical site. The shaft 292 of the ramrod 290 can be sized and shaped to have generally the same dimensions as the passageway. The ramrod 290 can push the flowable material down the funnel 294 through the second portion of the funnel stem 296 and into the nozzle 248. In some embodiments, at least a portion of the ramrod 290 can be flexible and/or compressible so that the ramrod 290 can conform to the contours of the bend in the funnel stem 296 as the ramrod 290 pushes the flowable material into the delivery tube 240. For example, the shaft 292 can be made of a rubber material and be flexible enough to bend in the funnel stem 296, but still provide sufficient rigidity to force the flowable material into the delivery tube 240.

In some embodiments, the device comprises a body, a delivery tube with a passageway in fluid communication with the body, an advancement mechanism for driving a rod distally into the passageway, and a lever to move the advancement mechanism. The advancement mechanism can comprise a gripping mechanism for gripping the driving rod while the lever drives the driving rod distally relative to the body. An example of a gripping mechanism is illustrated in FIG. 10. In some embodiments, the advancement mechanism comprises ratcheting teeth for incrementally ratcheting the driving rod distally as the lever is pulled proximally relative to the handle. Examples of a ratcheting mechanism are described herein and shown in FIGS. 8 and 9. The device can include a holding mechanism for resisting proximal motion of the driving rod while resetting the lever after lever activation. Examples of holding mechanisms are described herein. The device can have a rotating mechanism for allowing operator rotation of the delivery tube relative to the body. Examples of rotating mechanisms are described herein. The device can include a depth indicator for showing the depth to which the delivery tube is inserted by an operator. Examples of a depth indicator are described herein, and an example is shown in FIG. 3.

In a method of preparing a delivery tube 140 for use on a device 100, the delivery tube 140 can be filled with flowable material. A plug 198 can be secured to the distal end of the delivery tube 140 to block the exit opening of the nozzle 148 while the delivery tube 140 is packed with flowable material. The proximal end 144 of the delivery tube 140 can be fitted with a funnel 194, wherein a funnel sleeve 196 can engage the groove 146 on the proximal end 144 of the delivery tube 140 to secure the funnel 194 to the delivery tube 140.

Flowable material can be placed in the funnel 194 and directed through the bottom of the funnel into the passageway 142 of the delivery tube 140. In some embodiments, a ramrod 190 is used to push the flowable material into the passageway 142. The ramrod 190 can be used to move the flowable material toward the distal end of the delivery tube 140, and to compress the flowable material when desired. In some embodiments, the plug 198 has a vent, or the vent can be an opening disposed between the plug 198 and nozzle 148, so that air inside the delivery tube 140 can be expelled as the flowable material is placed in the passageway 142. The venting of the air can help to relieve pressure that may otherwise build up in the passageway 142, which can lead to resistance in inserting the flowable material.

After a desired amount of flowable material is placed in the delivery tube 140, the funnel 194 and/or plug 198 can be removed from the delivery tube 140 in preparation for attachment to the body 120. As discussed above, the delivery tube 140 can be attached to the body 120 in a plurality of orientations wherein the nozzle 148 is directed in one of several directions. As illustrated in FIGS. 3 and 4, the knob 150 of the delivery tube 140 can be coupled with the aperture 126 of the body 120 in various rotational orientations about its longitudinal axis 154. In the illustrated embodiment, the knob 150 has a hexagonal shape such that the delivery tube 140 can be inserted in six rotational orientations that are 60 degrees apart. In other embodiments, the delivery tube and aperture are configured to be coupled in increments of 5 degrees, 15 degrees, 30 degrees, 45 degrees, 60 degrees, 90 degrees, etc., or infinite adjustability. The user can select the orientation of the delivery tube 140 that places the exit opening of the nozzle 148 in the desired direction, while allowing easy operation of the lever 180 without obstruction from the patient's anatomy or other instruments.

The driving rod 160 can be inserted into the hole 124 and into the cavity 127 of the body 120. The driving rod 160 is positioned so that the at least one channel 168 is aligned with the at least one tab 138 in the hole 124. The alignment of the tab 138 and channel 168 can position the ratchet teeth 162 of the driving rod 160 in the correct orientation to engage the advancement mechanism 170 in the cavity 127. The driving rod 160 can be pushed distally until the ratchet teeth 162 engage the advancement mechanism 170. In some embodiments, the driving rod 160 is pushed through the cavity 127 and into the passageway 142 of the delivery tube 140 until the distal end of the driving rod 160 is near the flowable material in the delivery tube 140. The longitudinal axis 164 of the driving rod 160 is substantially aligned with the longitudinal axis 154 of the delivery tube 140 as the driving rod 160 is advanced through the passageway 142 of the delivery tube 140.

In some embodiments, a method of using the device 100 comprises inserting the delivery tube 140 into the surgical site. The delivery tube 140 can be inserted with the exit opening in the nozzle 148 directed in the desired direction for dispensing. In some embodiments, the delivery tube 140 has indications 152 that are used to realize the depth of the nozzle 148 from the patient's skin tissue. The indications 152 can measure the actual distance from the nozzle 148 along the delivery tube 140, or may indicate relative distances. In some embodiments, the delivery tube has a mark to show the direction of the exit opening on the nozzle 148 in case visualization of the nozzle 148 is obstructed. The user can then dispense the flowable material by actuating the lever 180 to move the driving rod 160 and push the flowable material out through the exit opening of the nozzle 148.

In some embodiments, a method for using the device comprises the step of applying a force to the lever 180 to move the lever 180 toward the second position. In some embodiments the body 120 comprises a handle 122 and a lever spring 182 coupled to the lever 180 and the handle 122, wherein the lever spring 182 opposes proximal movement of the lever 180 relative to the handle 122, and wherein the step of ratcheting further comprises the steps of releasing the force on the lever 180 and allowing the lever spring 182 to move the lever 180 toward the first position.

A method of using the device can comprise activating the advancement mechanism 170 wherein the activating comprises the step of ratcheting the driving rod 160 distally. The driving rod 160 can comprise a longitudinal axis 164 and a surface 166 with a plurality of angled ratchet teeth 162 on at least a portion of the surface 166. In such embodiments, the advancement mechanism 170 is coupled to a lever 180 capable of movement between a first position and a second position and mounted to the body 120 by a lever pivot 184. The advancement mechanism may further comprise a first ratchet pawl 172 coupled to the lever 180 and adapted to engage the ratchet teeth 162. The first ratchet pawl 172 may move the driving rod 160 distally relative to the body 120 as described herein. The drive mechanism may further comprise a second ratchet pawl 176 adapted to engage the ratchet teeth 162 and oppose proximal motion of the driving rod 160 relative to the body 120 as described herein.

A method of using the device can comprise gripping the driving rod 260 and moving the driving rod 260 distally. As described herein, the device 200 can have gripping elements 270, 274 that are configured to grip the driving rod 260. In some embodiments, the method comprises the step of applying a force to the lever 280 to move the lever 280 toward the second position. Moving the lever 280 toward the second position engages the first gripping element 270 to move the first gripping element 270 distally. The first gripping element 270 grips the driving rod 260 to move the driving rod 260 distally. In some embodiments, the method further comprises the steps of releasing the force on the lever 280 and allowing the first gripping spring 272 to move the first gripping element 270 proximally, which moves the lever 280 toward the first position. The second gripping element 274 grips the driving rod 260 to prevent the driving rod 260 from moving proximally as the first gripping element 270 moves proximally.

In some embodiments, a method of using the device 100 comprises rotating the delivery tube 140 before, during and/or after the device 100 is inserted to the surgical site. As described herein, the device 100 can have a collar 134 that can be rotated, which causes rotation of the delivery tube 140 about its longitudinal axis 154. Rotating the collar 134 changes the direction of the exit opening of the nozzle 148. In some situations, the user can rotate the collar 134 to affect the direction of the nozzle 148 during surgery and efficiently distribute the flowable material out of the nozzle 148 around the surgical site. For example, when inserting the delivery tube into the surgical site, a user can rotate the collar 134 so that the other parts of the device 100, such as the body 120, handle 122, and lever 180, are accessible and are not impeded by the patient's anatomy or other equipment. In another example, once the delivery tube 140 is inserted into the surgical site, the collar 134 can be rotated to redirect the exit opening in the nozzle and spread the discharge of the flowable material to more effectively fill in areas around implants, bones, and tissue.

In some embodiments, a method of using the device comprises bending the delivery tube. As discussed above, the delivery tube can be made of a flexible material and the user can bend the delivery tube to avoid obstacles and reach the surgical site. The delivery tube can be pliable and bend during the insertion of the delivery tube, or the delivery tube can be bent before inserting into the surgical site. In embodiments where the delivery tube is bent before insertion, the delivery tube can retain its bent shape until the user straightens the delivery tube. The driving rod can also be flexible so that when the driving rod is advanced into the bent delivery tube, the driving rod can bend to match the shape of the bent delivery tube.

Once the flowable material is delivered to the surgical site, the device 100 can be removed from the patient. The delivery tube 140 can be released from the body 120. In some embodiments, the delivery tube 140 is released by pushing the button to actuate the sliding sleeve 128. In other embodiments, the delivery tube is released by other uncoupling methods depending on the design, such as by unscrewing a threaded connection.

The driving rod can be removed by continuing to actuate the ratcheting mechanism or gripping mechanism until the driving rod is moved distally entirely through the body and exiting out the distal end of the body. In some embodiments, the driving rod can be removed by pulling out the driving rod manually, either in the distal or proximal direction. In some embodiments, the ratcheting mechanism or gripping mechanism can be disengaged so that the driving rod can be removed freely. For example, in some embodiments the driving rod can be rotated about its longitudinal axis such that a smooth surface of the driving rod contacts the ratcheting mechanism and the driving rod can be removed without obstruction from the ratchet teeth.

In some embodiments, the delivery tube and driving rod can be disposable and discarded after use. The delivery tube and driving rod may contact the patient and the flowable material during use and can be discarded for sterile purposes while the body and other parts of the device can be reused after sterilization. In other embodiments, the delivery tube and driving rod can be cleaned and sterilized for reuse. In some embodiments, the delivery tube can be prefilled with flowable material and then delivered to the user. A variety of kits can be produced that include a prefilled delivery tube and a complementary sized/shaped driving rod. Kits having different volumes for the delivery tube, different flowable materials, and/or different lengths and diameters of the delivery tube can be made available.

Although certain embodiments, features, and examples have been described herein, it will be understood by those skilled in the art that many aspects of the methods and devices illustrated and described in the present disclosure may be differently combined and/or modified to form still further embodiments. For example, any one component of the device illustrated and described above can be used alone or with other components without departing from the spirit of the present disclosure. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present disclosure. Thus, it is intended that the scope of the present disclosure should not be limited by the particular embodiments described above, but should be determined only by a fair reading of the claims that follow.

What is claimed is:
1. A device for injecting materials into a patient, the device comprising:
 a body comprising a handle, a lever, a rotatable collar and a cavity inside the body;
 a delivery tube comprising an anti-rotation feature, a passageway along a longitudinal axis, and a nozzle with a lateral opening, the delivery tube configured to releasably couple to the rotatable collar at a distal end of the body; and
 a driving rod configured to be inserted from a proximal end of the body and extend through the cavity and into the passageway;
 wherein the rotatable collar is configured to rotate the delivery tube about the longitudinal axis; and
 wherein the lever is configured to move the driving rod distally toward the delivery tube when the lever is actuated toward the handle.

2. A device for injecting materials into a patient, the device comprising:
 a body comprising a handle, a lever, and a rotatable collar;
 a delivery tube comprising an anti-rotation feature, a passageway along a longitudinal axis, and a nozzle with an opening, the delivery tube configured to couple with a distal end of the body; and
 a driving rod configured to be inserted into the body and extend into the passageway;
 wherein the rotatable collar is configured to rotate the delivery tube about the longitudinal axis; and
 wherein the lever is configured to move the driving rod distally when the lever is actuated toward the handle.

3. The device of claim 2, wherein the passageway of the delivery tube is configured to be filled with fusion-promoting material.

4. The device of claim 2, wherein the opening in the nozzle is a lateral opening.

5. The device of claim 2, wherein one or more of the delivery tube and driving rod are at least partially flexible.

6. The device of claim 2, wherein the driving rod comprises a plurality of ratchet teeth that are engaged by an advancement mechanism coupled to the lever.

7. The device of claim 2, further comprising a gripping element coupled to the lever that is configured to grab the driving rod when the lever is actuated.

8. The device of claim 2, wherein the delivery tube and driving rod are disposable.

9. The device of claim 2, wherein the driving rod is configured to move unidirectionally in the distal direction.

10. The device of claim 2, wherein the nozzle comprises an angled inner surface.

11. The device of claim 2, wherein the driving rod comprises at least one channel configured to align with at least one tab on the body.

12. The device of claim 2, wherein the delivery tube further comprises indications representing the depth of insertion of the delivery tube into a patient.

13. The device of claim 2, wherein the delivery tube further comprises a groove and the body further comprises a sliding sleeve configured to engage with the groove.

14. The device of claim 13, wherein the sliding sleeve comprises a protrusion configured to engage the groove of the delivery tube.

15. The device of claim 2, wherein the rotatable collar comprises a plunger with a ball that is configured to engage detents on the body.

16. The device of claim 2, wherein the rotatable collar is configured to rotate and hold the delivery tube in discreet rotational orientations.

17. The device of claim 2, wherein the anti-rotation feature comprises a knob configured to fit in a complementary cavity of an aperture of the body.

* * * * *